United States Patent [19]

Ando et al.

[11] 4,210,812
[45] Jul. 1, 1980

[54] X-RAY IMAGING DIAGNOSTIC APPARATUS WITH LOW X-RAY RADIATION

[75] Inventors: Shoichi Ando; Kiminobu Inaba; Tomoaki Yoshida, all of Tokyo, Japan

[73] Assignee: The Foundation: The Assn. of Japan General Denistry, Tokyo, Japan

[21] Appl. No.: 25,466

[22] Filed: Mar. 30, 1979

Related U.S. Application Data

[63] Continuation of Ser. No. 851,703, Nov. 15, 1977, abandoned.

[30] Foreign Application Priority Data

Jun. 2, 1977 [JP] Japan .................... 52-63941

[51] Int. Cl.² ............................................. G03B 41/16
[52] U.S. Cl. ............................ 250/416 TV; 250/402; 358/111
[58] Field of Search ............... 250/416 TV, 401, 402; 358/111

[56] References Cited

U.S. PATENT DOCUMENTS

| | | | |
|---|---|---|---|
| 3,622,785 | 11/1971 | Irwin | 250/416 TV |
| 3,745,245 | 7/1973 | Yunde | 250/416 TV |
| 4,137,454 | 1/1979 | Brandon | 250/416 TV |

Primary Examiner—Craig E. Church
Attorney, Agent, or Firm—Stevens, Davis, Miller & Mosher

[57] ABSTRACT

An X-ray imaging diagnostic apparatus emitting a low X-ray radiation dose is disclosed as comprising an X-ray generating source for exposing an object, an optical system having a fluorescent screen for receiving the X-ray image at an aperture portion thereof, a high sensitivity imaging device coupled directly to the optical system and receiving an X-ray image from the fluorescent screen for radiographing the X-ray image, a control unit for amplifying the output from the high sensitivity imaging device and for controlling the exposure time of X-ray radiation emitted from the X-ray generating source, an image storing memory circuit connected to the control unit for storing an image signal therefrom and a monitor circuit for displaying the image signal. The exposure time of the X-ray generating source is controlled to be at most less than 1/100 second by the control unit and the image of an object obtained on the fluorescent screen is imaged with a high resolution and a high sensitivity so that the resultant image can be recorded and monitored. The exposure time of the X-ray radiation is decreased as low as possible by using the high sensitivity imaging device, so that an X-ray radiation dose applied to a human body is lowered as compared to conventional X-ray diagnostic apparatus.

4 Claims, 5 Drawing Figures

X-RAY IMAGING DIAGNOSTIC APPARATUS WITH LOW X-RAY RADIATION

This is a continuation of application Ser. No. 851,703 filed Nov. 15, 1977 now abandoned.

BACKGROUND OF THE INVENTION

The present invention relates to an X-ray imaging diagnostic apparatus emitting a low X-ray radiation dose and, more particularly, to an X-ray imaging diagnostic apparatus in which an X-ray radiation dose from an X-ray generating source for diagnosing dental disease or the like is less than 2/100 of an X-ray radiation dose required for conventional X-ray radiographs using a photo film. An X-ray image of an object is focused into an image by a fluorescent screen which is arranged in front of an optical system so that the image can be photographed and recorded by a high sensitivity imaging device or observed on a monitor or the like.

At present, the X-ray diagnosis for dental disease is performed by radiographing directly on high sensitivity X-ray film inserted into an oral cavity. This method is frequently used in Japan and an approximation of the total number of pictures taken in 1974 is 89,000,000. The X-ray radiation dose required for radiographing a molar region of an adult is 310 mrad per radiograph. This value is larger than the radiation dose of about 60 mrad which is absorbed by a subject in the case of a chest radiograph. Even though conventional radiographing systems have been partially improved to reduce that radiation dose, it still remains much higher than is desirable.

While the use of a television system having an image amplifier has spread recently in clinics and the X-ray exposure does is extremely decreased with the system at the time of diagnostic fluoroscopy, conventional radiography and development techniques are still used for the purpose of high accuracy information confirmation.

SUMMARY OF THE INVENTION

An object of the present invention is to provide an X-ray imaging diagnostic apparatus emitting a low X-ray radiation dose in which an intraoral fluoroscopic image, which is different from an image obtained by the conventional image amplifier or X-ray image storage apparatus used in general clinics, is radiographed by a high sensitivity imaging device used in a television system and the obtained image is stored in an image storing memory circuit and reproduced on a monitor such as a cathode ray tube so that film developing time is eliminated and the affected region is directly viewed instantly for diagnosis.

Another object of the present invention is to provide an X-ray imaging diagnostic apparatus emitting a low X-ray radiation dose having a control unit for decreasing the X-ray ray radiation dose radiated to an affected region to at least 2/100 of the X-ray radiation dose used in a conventional X-ray diagnostic system.

A further object of the present invention is to provide an X-ray imaging diagnostic apparatus emitting a low X-ray radiation dose which can perform X-ray diagnosis with an X-ray dose of 1/100 of the dose required for the conventional radiography.

An X-ray imaging diagnostic apparatus emitting a low X-ray radiation dose according to the present invention comprises an X-ray generating source for exposing an object of an affected region, an optical system having a fluorescent screen for receiving an X-ray at an aperture portion thereof, a high sensitivity imaging device such as a SIT (silicon intensifier target) tube coupled directly to said optical system and receiving an X-ray image from the fluorescent screen for radiographing the X-ray image, the control unit for amplifying the output from the high sensitivity imaging device and for controlling the exposure time of the X-ray radiation from the X-ray generating source, an image storing memory circuit connected to the control unit for storing an image signal from said control unit, and a monitor circuit for displaying said image signal. The exposure time of the X-ray generating source is controlled to be at most less than 1/100 second by the control unit and the image of an object obtained on the fluorescent screen is imaged with a high resolution and a high sensitivity so that the resultant image can be recorded and monitored.

PREFERRED EMBODIMENTS OF THE INVENTION

A brief discussion of the prior art follows.

A proposal has been made in which an X-ray image is scanned by a camera tube so that a picture thus picked up is displayed on a cathode ray tube in a television receiver for diagnosis (see for example, CHAHIERS d'ODONTO-STMATOLOGIE TOME 7, No. 3, 1975).

Figure 5:
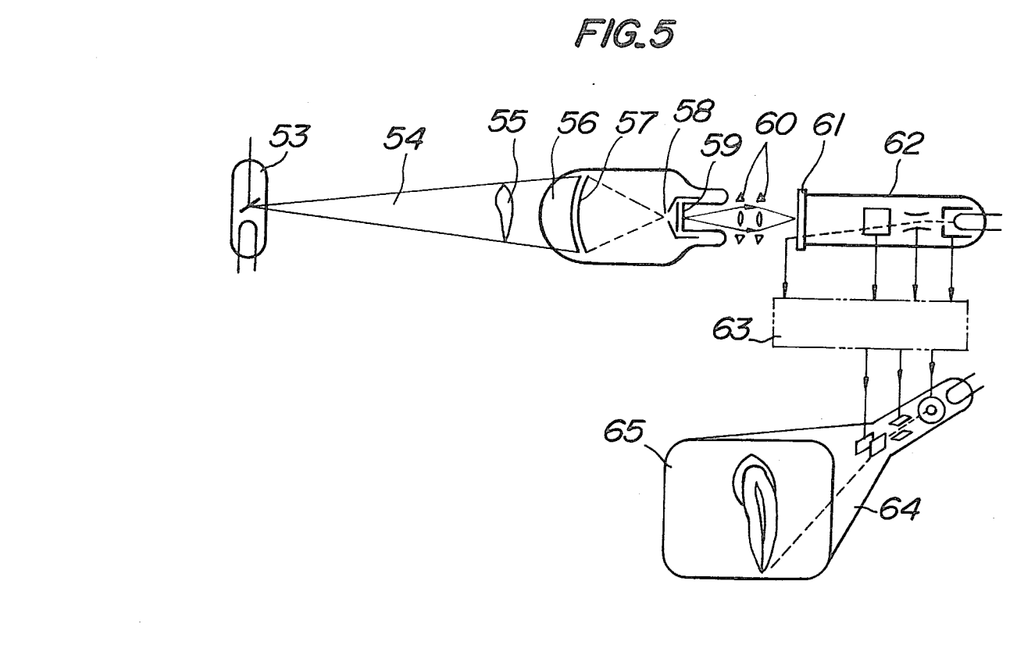
FIG. 5 is an explanatory diagram of one embodiment of a conventional dental diagnostic system in which a television system is utilized so that an image obtained from an X-ray emission can be viewed.

In such a system, as shown in FIG. 5, an X-ray beam 54 is radiated from an X-ray tube 53 to an object 55 such as a tooth. An X-ray beam which passes through the object is received by a photocathode 57 which forms a primary image receiving plane of an image intensifier 56 having an electron converging lens 58. An image produced by this X-ray radiation is photoelectrically converted into an electron beam image. This electron beam image is converged by an electron converging lens 58 so that a secondary image obtained from the converging lens 58 is projected onto a projection plate 59 arranged in front of an optical system of a vidicon camera tube 62. A bright secondary light image which is derived from the projection plate 59 is transmitted through an optical system 60 to a target 61 which is located at an image receiving portion of the camera tube 62. An electron change image (or electron change distribution) on the target 61 is scanned by a beam which is produced from an electron gun of the camera tube so that a television signal is obtained. This television signal is resolved, amplified, transmitted and reproduced to display a radiological scanning image on a picture tube 64. This system, however, is a theoretical proposal and is not practical since the resolution power in this system is far inferior to that of the present invention, and if use is made of their type of image intensifier, the dimensions and form of the image intensifier are too large thus preventing its insertion into a mouth in place of the usual photo film. A super high sensitivity camera tube cannot be used in the prior art because of possible unit damage so that a bright optical image should be projected on a projection screen in an optical system in front of the camera tube by amplifying an X-ray image by means of an electron converging system after the X-ray image is photoelectrically converted to an electron beam.

In the present invention, use is made of a screen having a coating thereon of fine grained and high resolution fluorescent material which can be inserted into a mouth similarly to an X-ray photo sensitive film for dental diagnosis so that an X-ray image obtained by a small X-ray radiation dose is resolved. An optical system which interrupts another light source is located in front of a super high sensitivity camera tube so that the X-ray image is received by the target of the super high sensitivity camera tube through the optical system and a photoelectric conversion is performed by the target. The exposure time of the X-ray emission is limited to a short time (1/100–1/1000 sec) so that a super high sensitivity camera tube such as a noctovisional image tube can be used. Thus, the exposure time of the X-ray emission is limited to as short a time as possible so that an X-ray radiation dose applied to a human body is reduced. The objects of the present invention are attained by a control system for controlling a beam scanning period of the super high sensitivity camera tube and the X-ray radiation period.

That is to say, the present invention accomplishes the following in order to reduce an X-ray radiation dose in the disclosed diagnostic system.

In order to convert a fluorescent image on a fluorescent screen to an electrical signal as efficiently as possible, the scanning of the television camera (camera tube) is stopped while the screen is luminous and the image is fully stored on the light receiving surface of the camera tube. p Accordingly, an afterglow time (several milli seconds) of the fluorescent screen is taken into consideration in determining a frame blanking time and the frame blanking time is determined to be longer by 10 milli seconds (or one pulse width) than the X-ray radiation time.

The light energy stored in the camera tube is fully converted to an electrical signal by scanning the light receiving surface twice by an electron beam. The electrical signal is further stored in an image memory unit such as a scanning converter.

The control circuit for controlling the exposure time of X-ray radiation and its functions are described as follows:

(1) A rectangular wave B (FIG. 4) is formed from an input signal A of commercial alternating line current, e.g., 100 V (50 Hz–60 Hz) by means of transistor zero biasing. This rectangular wave B is used as a time base for the control circuit. Further, one pulse width in terms of the frequency of the commercial alternating current source is 10 milli seconds.

(2) The pulses of this rectangular wave B are counted to produce a signal which is required in an X-ray television system which will be described hereinafter. The signal is transmitted to a television camera control and an X-ray tube.

A prime, i.e., initiation, signal C is formed in such a way that a time interval between the prime signal and the frame blanking signal is determined to be 200 msec by a reset signal D in a camera control and a image storing memory circuit.

The frame blanking signal D is a signal for stopping the scanning of the television camera. A delay of 10 msec is provided between this frame blanking signal and the starting point of the X-ray radiation signal.

A scanning start signal is a signal which starts the scanning of the television camera twice and has a delay of 10 msec from the termination of the X-ray radiation to the start of beam scanning.

A signal F is an X-ray radiation signal, the exposure time of the X-ray tube of which can be arbitrarily controlled in steps of 10 msec from 10 msec to 990 msec. The actual exposure tome is displayed on a two digit digital display.

(3) A sequence of operations in the diagnosis system according to the present invention is performed by pushing one push button switch. If the switch is pushed again during the sequence of operations, the whole sequence of operations is reset immediately. Further, each sequence may be reset by turning off the power supply of the control circuit (by means of the power switch).

(4) A triac is used for the switching of the X-ray tube so that a time delay does not occur. Further, a photo coupler is employed to drive the triac and also to isolate the power supply circuits between the control unit and the television camera cntrol and the X-ray tube.

Figure 1:
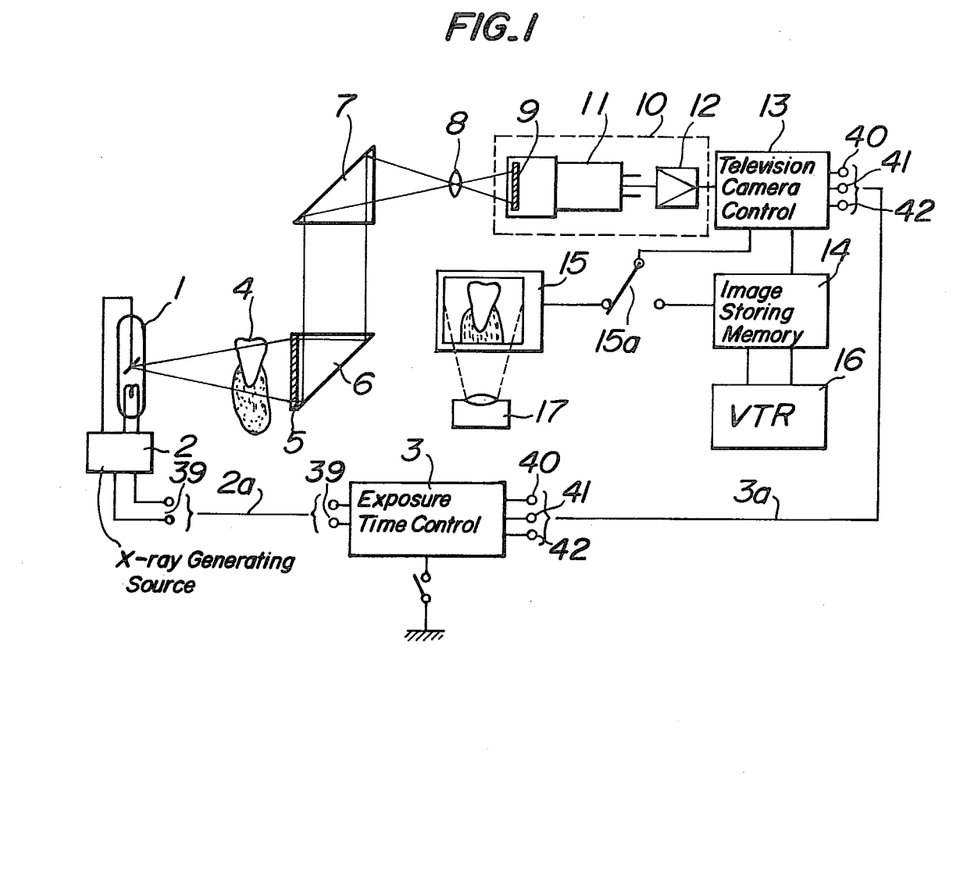
FIG. 1 is a block diagram showing an outline of an X-ray imaging diagnostic apparatus emitting a low X-ray radiation dose according to the present invention.

An X-ray imaging diagnostic apparatus according to the present invention will be explained with reference to the accompanying drawings. In FIG. 1, a reference numeral 1 denotes an X-ray tube, 2 is an X-ray generating source connected to the X-ray tube 1, 3 is an exposure time control circuit having a logic circuit formed by the combination of counter circuits for determining the exposure time of X-ray radiation of the X-ray tube 1. The control circuit 3 is connected to the X-ray generating source 2. A reference numeral 4 denotes a diagnostic object such as a tooth or jawbone, 5 is a fluorescent screen arranged over the front aperture of an optical system which receives impinging X-ray radiation from tube 1, 6 and 7 are prisms arranged at the rear of the fluorescent screen, 8 is a lens system, 9 is an image receiving portion such as a silicon plate provided in front of a high sensitivity imaging device 10, 11 is a camera tube, 12 is an amplifying unit including a preamplifier circuit, a deflection circuit, a high voltage circuit, a cathode circuit and so on, 13 is a television camera control circuit having an image amplifier, a synchronization circuit, a sequence circuit, a constant voltage power supply circuit and so on, 14 is an image storing memory device connected to the television camera control circuit 13, 15 is a monitor connected to the television control circuit 13, 16 is a recording apparatus such as a magnetic recording and reproducing apparatus having magnetic tape or magnetic cards as a storage medium and 17 is a camera for taking a picture of an image displayed on the monitor 15.

Operations of the X-ray imaging diagnostic apparatus according to the present invention will be described with reference to FIG. 1, in which the diagnostic object such as a tooth or jawbone is inserted between the X-ray tube 1 and the fluorescent screen 5. If the X-ray tube is energized, the X-ray image of the diagnostic object 4 is formed on the fluorescent screen 5. The image is projected to the image receiving portion 9 such as a silicon plate provided on the front surface of the high sensitivity camera tube through the prisms 6 and 7 and the lens system 8. The high sensitivity imaging device 10 uses a high sensitivity camera tube 11 having a silicon target (SIT) or a calnicon target and the image receiving portion 9 thereof uses the silicon plate or the like to which a high voltage is applied. If a light strikes upon this portion 9, a charge which is proportional to the amount of the received light is accumulated. If this silicon plate is scanned by the electron beam of the camera tube 11, a current flow which is proportional to the charge image is obtained. Since this silicon plate has an extremely high sensitivity, burning damage occurs if too much light is received. That is, if excessive charges are accumulated on the image receiving plate 9, the elements of the silicon plate are damaged. In view of this, the exposure time of X-ray radiation from the X-ray tube 1 is limited to under 1/100 second. Therefore, it is necessary that the camera tube be a high sensitivity type such as the SIT camera tube which has a high sensitivity amplification function. Accordingly, the present invention employs a high sensitivity camera tube such as the SIT camera tube to which the image storing memory device 14 such as a scanning converter is connected through the television camera control circuit 13. A changeover switch 15a is inserted between the television camera control circuit 13 and the image storing memory device 14 for changing from the memory device 14 to the monitor 15 or vice versa. That is to say, the image is stored in the image storing memory device 14 or is displayed on the image receiving surface of the cathode ray tube in the monitor 15 as a fixed still picture, depending upon the manual or automatic change of the changeover switch 15a. While the fixed still picture is observed for the purpose of diagnosis, this picture may be taken and recorded by a usual still picture camera, if required. If a disc memory apparatus or the like is connected to said image storing memory circuit, in plce of the video tape recorder 16, the record of diagnosis can be recorded on one sheet of magnetic disc. This method of recording is convenient for diagnosis purses. Instead of said video tape recorder, an analog to digital converter can be connected and the output from this analog to digital converter is supplied to a computer circuit for analizing the output.

According to the present invention, an X-ray image having a good picture quality can be captured on the screen of the monitoring cathode ray tube, when a fluorescent image is imaged by using the high sensitivity camera tube of SIT, the or of calnicon or the like in the X-ray diagnosis apparatus shown in FIG. 1. In order to record the image, a video tape recorder or a Polaroid camera can be used to obtain a clear monitoring image.

Figure 2:
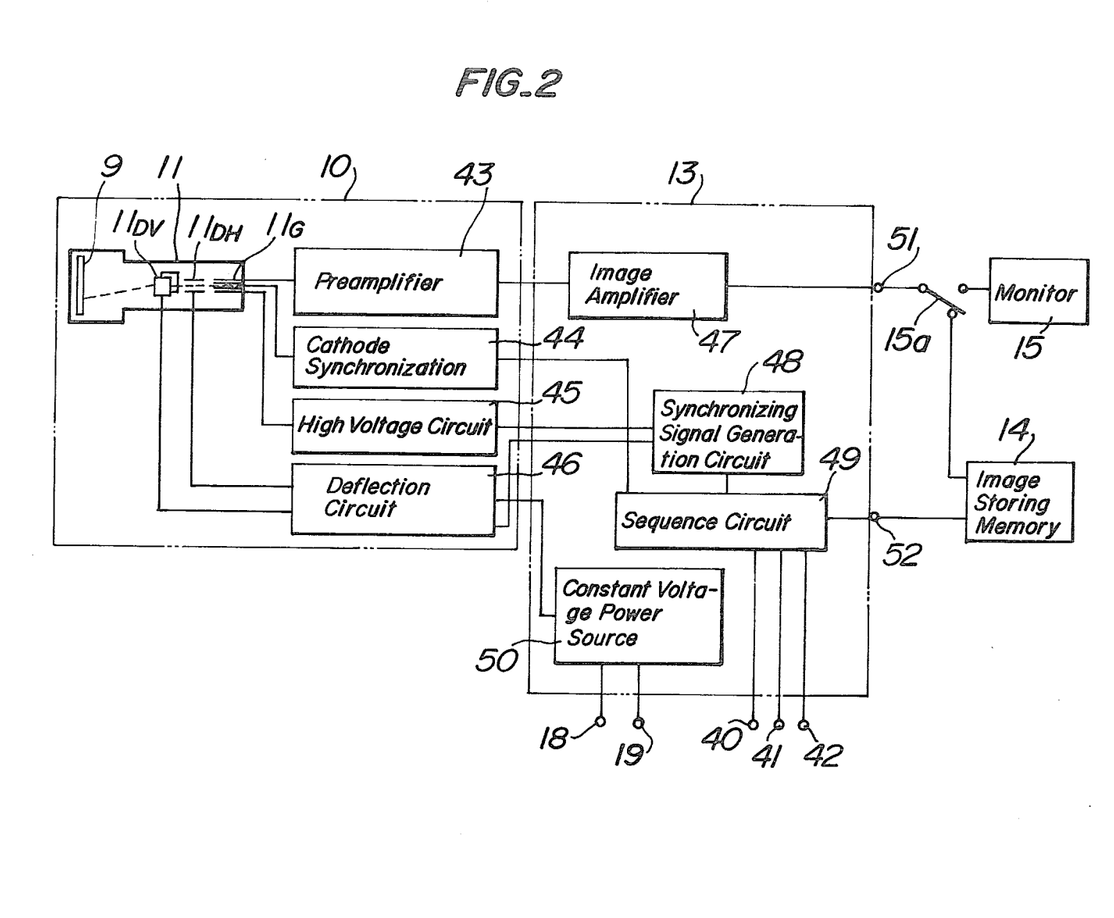
FIG. 2 is a detailed circuit diagram showing a high sensitivity imaging device used in the present invention.

FIG. 2 shows a detail of the high sensitivity imaging device 10 and the television camera control circuit 13 for controlling the imaging device 10. In the high sensitivity imaging device, 11DV denotes a vertical deflecting plate, 11DH is a horizontal deflecting plate, 11G is an electron gun, 43 is a preamplifier circuit, 44 is a cathode synchronizing circuit, 45 is a high voltage circuit and 46 is a deflecting circuit. In the television camera control circuit 13, a reference numeral 47 denotes an image amplifying circuit, 48 is a synchronizing signal generating circuit, 49 is a sequence circuit, 50 is a constant voltage power source, 40, 41, 42 are terminals connected to the exposure time control circuit 51, 52 are terminals connected respectively to the monitor 15 and the image storing memory device 14 and 15 is a contact of a changeover switch. This television camera control circuit 13 is essential to operate the camera tube 11. A SIT super high sensitivity camera tube using a silicon plate is the most preferable for the camera tube. However, as noted, a television camera tube using calnicon may also be used. The specific sensitivity between the calnicon and the SIT camera tube is 1:100-1000, so that an X-ray radiation dose can be limited to less than 1/100 of the dose encountered in a conventional X-ray photographing system.

Figure 3:
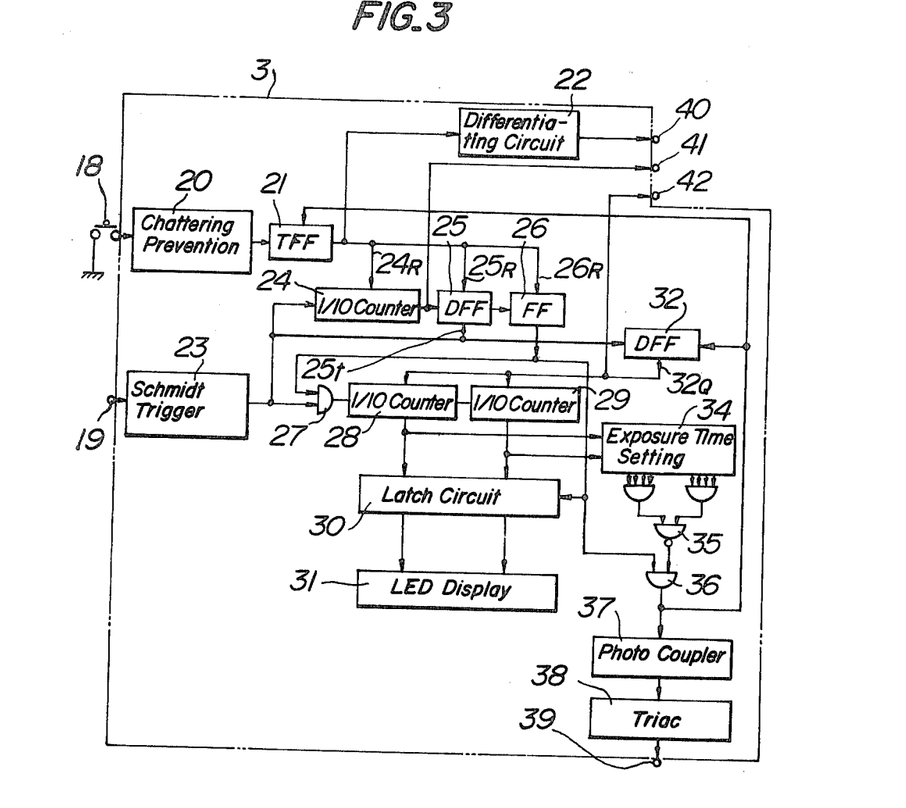
FIG. 3 is a detailed circuit diagram showing a control box for controlling the X-ray radiation time used in the present invention.

FIG. 3 shows a detailed circuit diagram of the control circuit 3 for controlling the exposure time of the X-ray radiation . In FIG. 3, a reference numeral 18 denotes a starting button switch for starting the operation of the whole control circuit 3. A reference numeral 19 denotes a terminal of a sinusoidal power supply source of 50 Hz. A reference numeral 20 denotes a chattering preventing circuit in which an input wave is shaped and then applied to a trigger flip-flop circuit 21, an output of which is supplied to a terminal 40 as a prime signal via a differentiating circuit 22. The sinusoidal wave applied from the terminal 19 is changed to a rectangular trigger waveform by a Schmidt trigger circuit 23. This trigger signal is applied to a decimal counter circuit 24, a delayed flip-flop circuit 32 and an AND circuit 27. When an output from the trigger flip-flop circuit 21 is applied to a reset terminal 24R of the decimal counter circuit 24, the decimal counter circuit 24 is reset and starts its counting. Then, the decimal counter circuit 24 produces an output signal as a frame blanking signal after 10 trigger signals from the Schmidt trigger circuit 23 are counted. This frame blanking signal is applied to a delayed flip-flop circuit 25 and a terminal 41. When the output from the decimal counter circuit 24 is applied to the delayed flip-flop circuit 25 and the reset signal is applied to a reset terminal 25R of the delayed flip-flop circuit 25, the delayed flip-flop circuit 25 transfer its output signal to a following reset flip-flop circuit 26 after a delay corresponding to one timing signal which is a trigger signal of 20 ms applied to a trigger terminal 25t of the flip-flop circuit 25 from the Schmidt trigger circuit 23. The output signal from the reset flip-flop circuit 26 is applid to one input terminal of an AND circuit 36. The other terminal of the AND circuit 36 has a positive voltage, so that this AND circuit 36 produces an AND output signal which triggers the X-ray tube 1 via a photo coupler circuit 37 and a triac circuit 38 causing the start of X-ray emission. The output signal from the reset flip-flop circuit 26 is also applied to the AND circuit 27. The other input terminal of the AND circuit 27 receives the output signal from the Schmidt trigger circuit 23, so that both of the input terminals of the AND circuit 27 receive positive voltages and that the AND circuit 27 produces an AND output signal which is applied to a decimal counter circuit 28. One output terminal of the decimal counter circuit 28 produces an output signal at every count, which output signal is applied to an exposure time setting switch 34. The other output terminal of the decimal counter circuit 38 produces another output signal at every ten counts which is applied to the following decimal counter circuit 29. If the decimal counter circuit 28 receives an input signal having a time duration of 10 ms, an output signal having a time duration of 100 ms is supplied to the decimal counter circuit 29 and an exposure time setting switching circuit 34. When the AND circuit 36 produces an output signal, a signal is supplied to the X-ray tube 1 from a terminal 39 and the X-ray tube 1 starts emitting radiation. When the AND circuit 36 produces a negative output thereafter, the trigger flip-flop circuit 21 and the delay flip-flop circuit 32 produce negative outputs, so that the trigger flip-flop 21 is reset and interrupted. Since the delay flip-flop circuit 32 receives the output signal from the Schmidt trigger circuit 23, the decimal counters 28 and 29 are reset after 10 ms. When the reset flip-flop circuit 26 is reset, the one input signal of the AND circuit 27 becomes negative. The delay flip-flop circuit 32 counts one trigger signal from the Schmidt trigger circuit 23 after the interruption of the output signal from the AND circuit 36 is detected. The decimal counter circuits 28 and 29 are reset by an output signal which is delayed by one count (10 ms) and derived from an output terminal 32Q. During this delay time, the output signals from the decimal counter circuits 28 and 29 are applied to a LED display device 31 through a latch circuit 30 so as to display an exposure time. Once the latch circuit 30 detects the interruption of the AND circuit 36, the circuit 36 holds its operating condition. In view of this, the decimal counter circuits 28 and 29 are stopped after one count. In this way, the LED display device 31 can hold its display of the exposure time.

Figure 4:
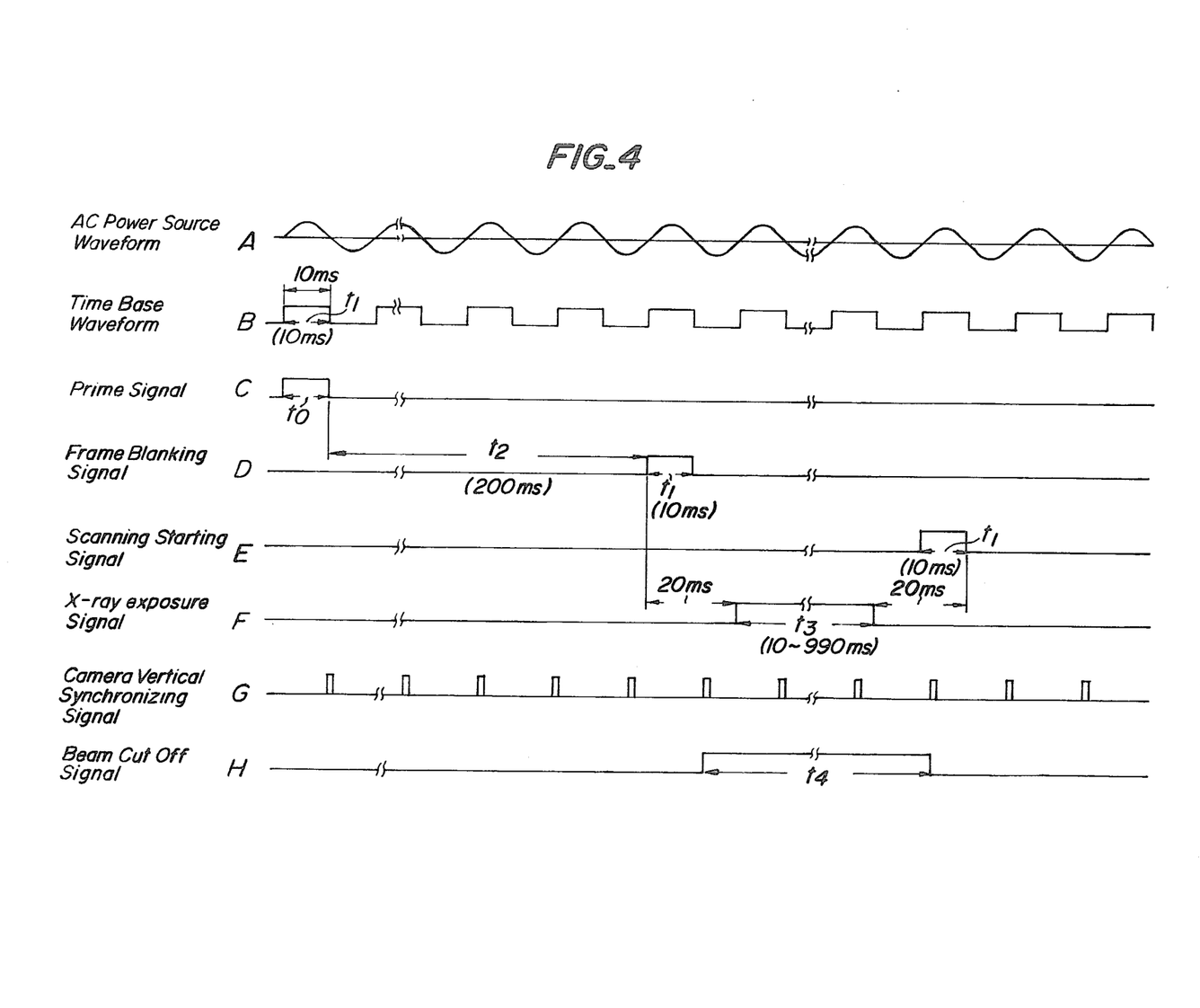
FIG. 4 is a waveform diagram illustrating various waveforms at various parts of the controlling circuit which is used to explain the principle of the present invention.

This relation is illustrated in FIG. 4. In FIG. 4, a waveform A shows the input signal having a commercial line frequency of 50–60 Hz. A waveform B shows the output signal (rectangular waveform) from the Schmidt trigger circuit 23. A waveform C shows a prime signal waveform at the terminal 40, D is a frame blanking signal waveform existing at a terminal 41, E is a scanning starting signal waveform at a terminal 42, F is an exposure time setting signal which is applied to the X-ray generating circuit 2, G is a vertical synchronizing signal waveform generated by the synchronizing signal generating circuit 48 in the television control circuit and H is a signal for interrupting a signal from a synchronizing signal generating circuit 48 to the cathode synchronizing circuit 44. The above interruption is made by a beam cut off signal produced at a sequence circuit 49. The prime signal C is produced immediately after the push button switch 18 is activated. The frame blanking signal D is produced at a given time after the production of the prime signal C. This time period is assumed to be $t_2$ and this $t_2$ is equal to 200 ms. This prime signal C is supplied to the image storing memory device 14 through the television camera control circuit 13 which is set to a store condition. In order to achieve this store condition, a delay time of 200 ms is required in the frame blanking signal D. This delayed frame blanking signal D is applied to the television camera control circuit 13 in which a beam cut off signal H is produced from an instant at which the first camera vertical synchronizing signal G is applied. The beam cut off signal H cuts off a cathode beam circuit 45 in the high sensitivity camera tube 11, so that the scanning for reading out said camera tube 11 is interrupted. The optical system connected to this camera tube 11 is shielded at the position of the fluorescent screen 5 and the light image is not transferred unless the X-ray impinges upon the fluorescent screen 5. If the vertical synchronizing signal G of the television camera is first picked up, the beam cut off signal H is generated. The reason of such a beam cut off operation follows. Unless the beam which is applied to the silicon plate for use in the target of the camera tube is interrupted for a suitable time corresponding to the X-ray radiation time a storage time is not provided which is sufficient to store enough of the electric charge in the silicon plate of the image receiving portion 9 in the camera tube 11. This relation can be explained by a relationship between the X-ray exposure time $t_3$ and the beam cut off period $t_4$. The time period from the leading edge of the frame blanking signal to the leading edge of the X-ray exposure signal F is chosen to be 20 ms. The reason for this 20 ms follows. While the frame blanking signal D is synchronous with the input signal A and the trigger signal B, the camera vertical synchronizing signal G is not synchronous with those signals at all, so that if the frame blanking signal D is in synchronism with the X-ray exposure signal F, it may happen that the production of the first vertical synchronizing signal G is delayed from an instant at which the X-ray exposure signal F is produced. As a result, the production of the beam cut off signal H is delayed, so that there may be the possibility that a sufficient amount of charge for receiving a light image is not stored in the silicon plate. The X-ray exposure time $t_3$ is set by the exposure time setting switching circuit 34 and can be easily adjusted to a suitable length. Further, the time period $t_4$ starts a few milli seconds earlier than the time period $t_3$. The scanning starting signal E is formed with some delay after the instant that the time period $t_3$ is terminated. This scanning starting signal E is applied to the television camera control circuit 13 in which the first synchronizing signal G is picked up and the beam cut off signal H is interrupted under the control by means of the sequence circuit 49. Further, there is provided a time difference of ten odd milli seconds between the terminating instant of the period $t_3$ and the terminating instant of the period $t_4$ in order to capture a poor light beam which is produced in an afterglow time of the fluorescent substance 5 by the X-ray radiation.

The following results are obtained when the X-ray imaging diagnosis apparatus according to the present invention is used for diagnosis.

(1) The chosen imaging field size is 22 mm$\phi$. This size could sufficiently cover a multi-rooted molar whose X-ray image is obtained on the monitor simultaneously with the operation of the apparatus. Accordingly, X-ray picture development is not required.

(2) The picture image thus recorded does not deteriorate after a one-hour continuous test.

(3) According to data with respect to mandibular bone water phantom in a condition equivalent to a condition of use in a human body, a single dose exposure by the apparatus according to the present invention is about 1/60 through 1/120 of that of the prior art imaging apparatus or about 2.6 mrad through 5.2 mrad (Table I).

(4) Either one of a positive or negative television picture image can be selected for detailed examination by one operation of changeover switch. When an enlarged pictured is required for an examination, enlargement and conversion of object position can be made by a zoom operation without using a magnifying lens.

(5) In order to get a permanent record, a monitor image is photographed by a usual still picture camera or Polaroid (trade name) camera. In other words, the present invention provides a new television system for X-ray imaging apparatus in which an intraoral fluoroscopic image can be imaged instantly with a very small X-ray radiation dose and the following advantageous effects are obtained.

(a) Information from an X-ray diagnosis is immediately obtained.
(b) The same diagnosis effect is obtained even though an exposure dose is decreased to 1/60 through 1/100 of the usual dosage.
(c) A ratio of information pick-up is greatly enhanced relative to the conventional X-ray film by adjusting the gain and brightness controls of the monitor, so that the resolving power of this television system has a large latitude.

Table 1

|  | Conventional system | Improved system | The present invention |
| --- | --- | --- | --- |
| Radiation dose | 310 mrad | 1/5 through 1/6 (250 mrad through 280 mrad) | 1/60 through 1/100 (2.6 mrad through 5.2 mrad) |

While in a television system use is generally made of video tape as recording medium, there is a disadvantage that a reproducing operation is rather complicated. In view of this, the present invention employs an image storing memory circuit which is connected to an output circuit of a camera tube, so that a television picture is retained for diagnosis by storing the picture for about 1 through 3 hours.

While in the above embodiment of the present invention the optical system having the prism, lens, mirror and so on is employed in FIG. 1, it is practical to use an optical system having optical fiber for dental diagnosis. In this case, the optical system should shield external light.

According to the present invention, an absorbed X-ray dosage level is reduced to less than 2/100 of the dosage level absorbed in a conventional X-ray radiograph techniques using a high sensitivity radiograph film, and the obtained fluoroscopic image is captured by the optical system and imaged by the high sensitivity television camera. As a result, a television image is realized which can be viewed for diagnosis under day light conditions by using a high sensitivity television camera tube such as a super high sensitivity camera tube (SIT), even if the light emission energy of a fluoroscopic image is weak. This image can exist only within a very short X-ray exposure time (less than 1/100 second), so that the image is stored in the image storing memory circuit incorporated in the television camera control unit so as to fix the image on the screen of the cathode ray tube in the monitor circuit for about 30 minutes for diagnosis purposes. Accordingly, the development of a picture image is not required in contrast to prior art X-ray imaging techniques. Thus, diagnosis can be immediately undertaken after an easily recorded television picture is produced, so that precise and fast diagnosis can be realized.

In the case of dental diagnosis, an X-ray radiation source is located in the vicinity of a human body of a patient and it is necessary to take a picture of a tooth or mandibular region, so that it is absolutely necessary to set an X-ray radiation exposure time to less than 1/100 second. The present invention can satisfy this requirement or of shortening an X-ray exposure time by means of the high sensitivity camera tube for taking a fluoroscopic picture which is converted to a television signal which is then stored on a magnetic disc or the like so that an image can be directly viewed on the screen of the monitoring cathode ray tube. Thus, the present invention is very advantageous in that precise and fast diagnosis is realized.

Further, the beam cut off signal for the camera tube is produced just prior to the production of the X-ray radiation signal and is terminated slightly after the termination of the X-ray radiation signal. For that purpose, the logic circuit in the present invention is so arranged that the start and termination of the synchronizing signals of the beam cut off signal are controlled by the frame blanking signal and the scanning starting signal. As a result, the silicon plate used in the image receiving portion of the super high sensitivity camera tube is not subject to being damaged. Even though the X-ray exposure time is fixed at less than 1/100 second by controlling the synchronizing signals for controlling the beam scanning period of the camera tube and the X-ray exposure period of the fluorescent substance by means of the frame blanking signal and the scanning starting signal, respectively, it is possible to realize high sensitivity imaging. In addition, the image which is produced for dental diagnosis can be recorded on a magnetic disc or tape and can be displayed on the screen of the monitoring cathode ray tube, when required. Accordingly, the present invention provides a very useful image diagnosis apparatus.

According to the present invention, the skin of a patient receives an absorption dosage level of about 5 milli rem when the X-ray is exposed for 2/1000 second. In the case of 1/100 second exposure, the absorption dosage level is about 2.5 milli rem, and in the case of 1/1000 second exposure, the absorption dosage level is 0.5 milli rem. The radiation dosage level is approximately less than 1/60 of the case where the same skin tissue is imaged using an existing high sensitivity film and approximately less than 1/100 of the case where the same skin tissue is imaged by a conventional radiograph film. Thus, the present invention requires only a small absorption dosage.

In addition, according to the present invention, it is possible to reduce a required dimension of irradiation exposure to about 1/9 of the conventional dimension, so that the total absorption dose can be reduced remarkably.

At present, the exposure dose of dental radiography is of such a magnitude that 15 out of every 100,000,000 people are subject to cancer when radiographed once a year and that 0.08 out of 100,000,000 people are subject to a congenital hazard. This emphasizes the importance of reducing the exposure dosage absorbed by a human body.

In view of this, it is desirable to reduce the exposure dosage as much as possible to reduce the radiation hazard. According to the present invention, the required exposure dose is reduced to less than 1/100 of the exposure dose encountered in conventional radiographic techniques, so that these hazards can be substantially reduced.

Furthermore, the present invention realizes a precise image for analysis, compared images obtained by prior art radiographic techniques, in addition to the omission of the X-ray film developing process. The image, according to the present invention, can be enlarged, changed in contrast or solarized by operating one push button switch.

What is claimed is:
1. An X-ray image diagnostic apparatus having a low X-ray radiation dosage level comprising:

an X-ray generating source for emitting radiation to expose an object;

an optical system having a fluorescent screen at an entrance thereof for receiving said emitted X-ray radiation;

an imaging device comprising a television camera tube having an image intensifier target and a high voltage supply and deflection synchronizing and blanking circuits coupled directly to said optical system for receiving an X-ray image from said fluorescent screen and forming a video signal image from said fluorescent screen image;

a television camera control unit for amplifying the output from said imaging device, said television camera control unit including a sequence circuit for controlling the supply of synchronizing signals to said camera tube;

an exposure time control circuit for controlling the exposure time of the X-ray radiation emitted from said X-ray generating source so that it is less than 1/100 second;

an image storing memory circuit connected to said television camera control unit for storing an image signal from said control unit; and, a monitor circuit for displaying said image signal, said X-ray exposure time control circuit comprising:

a chattering preventing circuit for shaping an input signal to a rectangular pulse train wave form which serves as a time base wave, a trigger flip-flop circuit for receiving said rectangular time base wave signal, a differentiating circuit for receiving said rectangular time base wave signal and supplying an initiation signal to said sequence circuit, a schmidt trigger circuit for changing a sinusoidal wave form from a power source to a rectangular trigger wave form, a first decimal counter circuit having an input receiving said rectangular trigger wave form and a reset terminal connected to said trigger flip-flop circuit for supplying a frame blanking signal obtained at its output terminal to said sequence circuit, a first delay flip-flop circuit having a reset terminal connected to output terminals of said schmidt trigger circuit, said first decimal counter circuit and said trigger flip-flop circuit, a following reset flip-flop circuit connected to the output terminal of said first delay flip-flop circuit after a delay corresponding to one pulse wave and for supplying a delayed output signal, a first AND circuit for receiving the output signals of said reset flip-flop circuit and said schmidt trigger circuit, a second decimal counter circuit for receiving the output signal from said first AND circuit, a third decimal counter circuit for receiving the output signal from said second decimal counter circuit, a second delay flip-flop circuit connected to the output of said schmidt trigger circuit for supplying an output signal forming a scanning starting signal supplied to said second and third decimal counters and said sequence circuit, a LED display device connected to said second and third decimal counter circuits through a latching circuit for displaying an exposure time, and an exposure time setting switching circuit connected to the outputs of said second and third decimal counter circuits for producing an exposure time setting switching signal and transferring it through second and third AND circuits to said X-ray tube so as to start X-ray emission.

2. An X-ray image diagnostic apparatus having a low X-ray raditation dosage level comprising:

an X-ray generating source for emitting radiation to expose an object;

an optical system having a fluorescent screen at the entrance thereof for receiving said emitted radiation;

an imaging device comprising a television camera tube having an image intensifier target coupled directly to said optical system for receiving an X-ray image from said fluorescent screen, a preamplifier for preamplifying the output from said camera tube, a cathode synchronizing circuit for supplying a synchronizing signal to a cathode of said camera tube, a high voltage circuit for supplying a high voltage to an electron gun of said camera tube to generate a scanning beam for said target, and a deflection circuit for supplying a vertical signal and a horizontal signal to respective vertical and horizontal deflecting plates in said camera tube;

an X-ray exposure time control circuit for controlling an exposure time of X-ray radiation emitted from said X-ray source to be less than 1/100 second and including means for generating a scanning start signal and a frame blanking signal which are timed relative to the exposure timing of said X-ray generating source;

a television camera control unit comprising an image amplifier for amplifying the output from said imaging device, a synchronizing signal generating circuit for supplying a camera vertical synchronizing signal to said cathode synchronizing circuit, a sequence circuit for generating a beam cut off signal and for interrupting the supply of a signal from said synchronizing signal generating circuit to said cathode synchronizing circuit under control of said beam cut off signal, and a constant voltage power source for supplying a constant voltage to said deflection circuit, said sequence circuit being responsive to said frame blanking signal and scanning starting signal to generate signals corresponding to the start and termination of said beam cut off signal in such a way that said beam cut off signal is generated slightly prior to the generation of an X-ray exposure and is terminated slightly after the termination of X-ray exposure;

an image storing memory circuit connected to said television camera control unit for storing an image signal received from said camera tube; and a monitor circuit for displaying said image signal.

3. An X-ray image diagnostic apparatus having a low-X-ray radiation dosage level comprising;

an X-ray generating source for emitting radiation to expose an object;

an optical system having a fluoescent screen at the entrance thereof for receiving said emitted radiation;

an imaging device comprising a television camera tube having an image intensifier target coupled directly to said optical system for receiving an X-ray image from said fluorescent screen, a preamplifier for preamplifying the output from said camera tube, a cathode synchronizing circuit for supplying a synchronizing signal to a cathode of said camera tube, a high voltage circuit for supplying a high voltage to an electron gun of said camera tube to generate a scanning beam for said target, and a deflection circuit for supplying a vertical signal and a horizontal signal to respective vertical and horizontal deflecting plates in said camera tube;

an X-ray exposure time control circuit for controlling an xposure time of X-ray radiation emitted from said X-ray source to be less than 1/100 second and including means for generating a scanning start signal and a frame blanking signal which are timed relative to the exposure timing of said X-ray generating source, said X-ray exposure time control circuit comprising:

a chattering preventing circuit for shaping an input signal to a rectangular pulse train wave form which serves as a time base wave, a trigger flip-flop circuit for receiving said rectangular time base wave signal, a differentiating circuit for receiving said rectangular time base wave signal and supplying an initiation signal to said sequence circuit, a schmidt trigger circuit for changing a sinusoidal wave form from a power source to a rectangular trigger wave form, a first decimal counter circuit having an input receiving said rectangular trigger wave form and a reset terminal connected to said trigger flip-flop circuit for supplying a frame blanking signal obtained at its output terminal to said sequence circuit, a first delay flip-flop circuit having a reset terminal connected to output terminals of said schmidt trigger circuit, said first decimal counter circuit and said trigger flip-flop circuit, a following reset flip-flop circuit connected to the output terminal of said first delay flip-flop circuit and said trigger flip-flop circuit for receiving an output signal from said first delay flip-flop circuit after a delay corresponding to one pulse wave and for supplying a delayed output signal, a first AND circuit for receiving the output signals of said reset flip-flop circuit and said schmidt trigger circuit, a second decimal counter circuit for receiving the output signal from said first AND circuit, a third decimal counter circuit for receiving the output signal from said second decimal counter circuit, a second delay flip-flop circuit connected to the output of said schmidt trigger circuit for supplying an output signal forming a scanning starting signal supplied to said second and third decimal counters and said sequence circuit, a LED display device connected to said second and third decimal counter circuits through a latching circuit for displaying an exposure time, and an exposure time setting switching circuit connected to the outputs of said second and third decimal counter circuits for producing an exposure time setting switching signal and transferring it through second and third AND circuits to said X-ray tube so as to start X-ray emission;

a television camera control unit comprising an image amplifier for amplifying the output from said imaging device, a sychronizing signal generating circuit for supplying a camera vertical synchronizing signal to said cathode synchronizing circuit, a sequence circuit for generating a beam cut off signal and for interrupting the supply of a signal from said synchronizing signal generating circuit to said cathode synchronizing circuit under control of said beam cut off signal, and a constant voltage power source for supplying a constant voltage to said deflection circuit, said sequence circuit being responsive to said frame blanking signal and scanning starting signal to generate signals corresponding to the start and termination of said beam cut off signal in such a way that said beam cut off signal is generated slightly prior to the generation of an X-ray exposure and is terminated slightly after the termination of X-ray exposure;

an image storing memory circuit connected to said television camera control unit for storing an image signal received from said camera tube; and a monitor circuit for displaying said image signal.

4. An X-ray imaging diagnostic apparatus as claimed in claim 3 wherein said image intensifying target comprises an image intensifying silicon target having a high voltage supply.

* * * * *